US006833912B2

(12) United States Patent
Lei et al.

(10) Patent No.: US 6,833,912 B2
(45) Date of Patent: Dec. 21, 2004

(54) APPARATUS FOR TESTING THE STATE OF AN ENDOSCOPE

(75) Inventors: Fang Lei, Durchhausen (DE); Jürgen Rudischhauser, Tuttlingen (DE); Jörg Weitzel, Liptingen (DE); Volker Preuss, Constance (DE)

(73) Assignee: Karl Storz GmbH & Co. KG (DE)

( * ) Notice: Subject to any disclaimer, the term of this patent is extended or adjusted under 35 U.S.C. 154(b) by 130 days.

(21) Appl. No.: 09/946,990

(22) Filed: Sep. 5, 2001

(65) Prior Publication Data

US 2003/0100818 A1 May 29, 2003

(30) Foreign Application Priority Data

Sep. 6, 2000 (DE) .................................... 200 15 447 U
Sep. 6, 2000 (EP) ........................................... 00119287

(51) Int. Cl.[7] .............................. G01B 9/00; A61B 1/00
(52) U.S. Cl. ..................... 356/124; 356/243.1; 600/102
(58) Field of Search .............................. 356/124, 243.1, 356/243.4; 600/102; 385/137, 58; 382/141

(56) References Cited

U.S. PATENT DOCUMENTS

| 4,613,232 | A |   | 9/1986  | Diener ........................ 356/124   |
| 5,820,547 | A |   | 10/1998 | Strobl ......................... 600/127   |
| 5,841,525 | A |   | 11/1998 | Rosow ..................... 356/124.5      |
| 5,966,210 | A | * | 10/1999 | Rosow et al. ................ 356/213     |
| 6,381,013 | B1 | * | 4/2002  | Richardson ................. 356/305     |

FOREIGN PATENT DOCUMENTS

| GB | 2 215 077 A  | 2/1998 |
| WO | WO 98/41836  | 3/1997 |

* cited by examiner

Primary Examiner—Gregory J. Toatley, Jr.
Assistant Examiner—Roy M. Punnoose
(74) Attorney, Agent, or Firm—St. Onge Steward Johnston & Reens LLC

(57) ABSTRACT

An apparatus for testing the state of the optical system of an endoscope comprises a first supporting device for the endoscope, a test pattern and a second supporting device for the test pattern, wherein the test pattern comprises a pattern, which allows a check of the actual viewing direction and of the actual field of view angle within tolerance values.

73 Claims, 2 Drawing Sheets

APPARATUS FOR TESTING THE STATE OF AN ENDOSCOPE

BACKGROUND OF THE INVENTION

The invention relates to an apparatus for testing the state of the optical system of an endoscope, comprising a first supporting device for the endoscope, a test pattern and a second supporting device for the test pattern.

Such an apparatus is known from U.S. Pat. No. 5,820,547.

An endoscope is particularly used in minimal-invasive surgery as a viewing instrument in order to be able to control from the outside an operation performed through a small incision in the body.

Endoscopes are, however, not only used in medical applications, but also in technical applications, e.g. for observing cavities in machines, combustion chambers of engines and the like, which cannot be observed with the naked eye.

The main element of an endoscope is its optical system. The optical system of an endoscope consists of rod lenses or glass fibers and objective lenses and eyepiece lenses. An endoscope can, additionally, comprise a light conducting system for illuminating the area to be observed. There is a plurality of endoscope types, which differ from each other by their endoscope-specific basic data. Such endoscope-specific basic data are e.g. the angle of view or the viewing direction and the field of view angle of an endoscope. Furthermore, endoscopes can also differ by the magnification ratio of the optical imaging and, moreover, by their geometrical dimensions.

With reference to the viewing direction of the endoscope, there are endoscopes with a straight forward viewing direction, i.e. the viewing direction of the endoscope forms an angle of 0° with the longitudinal axis of the shaft of the endoscope. There are also endoscopes with an oblique view optic, i.e. the viewing direction of the endoscope runs then in an oblique fashion with respect to the longitudinal axis of the shaft in a predetermined angle.

The optical system of an endoscope can be impaired by external influences in the course of time, so that the quality of the image transmission by the optical system is deteriorated and/or deviations of the nominal values of the basic data occur. Medical endoscopes in particular are sterilized after each use, the endoscopes being exposed to hot vapor under high pressure in an autoclave to this end. But also mechanical influences like impacts onto the shaft, e.g. when the endoscope falls down, may impair the optical system of the endoscope.

It is, thus, necessary to revise and/or to repair the endoscope after some time. There is the problem herewith that, if the reparation is improperly performed by not authorized workshops, the initial original state and/or quality standard of the optic is not achieved. For the manufacturer of the endoscope, there is, thus, the need, due to the requirements of customer service, to be able to check the state of the endoscopes with reference to their basic data in a quick and simple manner at least with reference to quality within acceptable tolerances. This includes, besides the qualitative check of the viewing direction and of the field of view angle, e.g. a qualitative estimation of the sharpness and/or of the contrast of the image transmission in the image center and/or in the border region of the image and, if necessary, a check of the state of the light conducting system, should the endoscope be equipped with such a system.

In U.S. Pat. No. 5,820,547 mentioned above, a portable apparatus that is simple in design for testing the state of the optical system of an endoscope is described, which comprises a supporting device for the endoscope to be examined and a test pattern and a supporting device for the test pattern. The supporting device for the endoscope consists of a cylindrical adapter comprising an axial central through bore, into which the distal end portion of the endoscope is inserted. For endoscopes with an oblique view optic, two lateral through bores that run obliquely to the longitudinal axis of the tube are provided, into which these endoscopes can be suitably inserted. The test pattern is fixed at a supporting device, which is firmly connected with the supporting device for the endoscope. The test pattern consists of an arrangement of line patterns of different line thickness, of a line grid and of an arrangement of concentric circles.

While this known apparatus is very simple in design, it has, however, the disadvantage not to be universally adapted to a plurality of different optical systems of endoscopes. For example, the distance between the test pattern and the distal end of the endoscope is firmly predetermined. As the distance between the test pattern and the distal end of the endoscope is firmly predetermined, in an observation of the test pattern through the endoscope, in dependency of the field of view angle, circle sectors of different sizes are seen, respectively, what makes the evaluation of the test more difficult for a user who is not trained technically. Moreover, only endoscope optics with three different viewing directions that are firmly predetermined on the adapter can be tested. The accuracy of the test, apart from that, is low. A check of the function of the light conducting system of the endoscope exceeding this test is not possible.

On the other hand, from U.S. Pat. No. 5,841,525, an apparatus for testing the state of the optical system of an endoscope is known, which is, however, very expensive and which requires periphery equipment like image processing equipment and a computer station for the evaluation of the test. This apparatus is, thus, not transportable and is not suited for performing a quick test in a different location at a customer's.

Further, U.S. Pat. No. 4,613,232 discloses a portable measuring device for testing optical systems of an endoscope consisting of a base plate, a rail with a longitudinally extending V groove for receiving a portion of the endoscope being mounted to extend parallel to the plate on a carriage movable at right angles to the groove. The device includes a vertical shaft mounted on the plate and terminating at one end in a conical point, and the shaft carries at least one extension arm which is mounted to pivot in a plane parallel to the base plate. Each arm adjustably supports a measuring disk which can have its height above the plate changed or its distance from the shaft changed. This known apparatus comprises a measuring disk having known scales and the like, whereby it is possible to exactly measure the angular field, the sight line, the diameter of the exit pupil, the subject field illumination, the depth of field, the focusing range, the visual lens magnification, the distortion and the resolution of the optical system of the endoscope being tested.

The invention has, thus, the object to improve an apparatus of the type mentioned at the outset in such a way that it allows a quick assessment of the quality and a check of the basic data and/or the image quality without time-intensive training of the user.

SUMMARY OF THE INVENTION

According to the invention, the object underlying the present invention is achieved with an apparatus for testing the state of an optical system of an endoscope having a viewing direction and a field of view angle, said apparatus comprising a first supporting device for said endoscope, a test pattern and a second supporting device for said test pattern, wherein said test pattern comprises a pattern, which allows a common check of an actual viewing direction and of an actual field of view angle of said optical system of said endoscope within tolerance values of a nominal value of said viewing direction and a nominal value of said field of view angle.

With this embodiment of the test pattern, the viewing direction and the field of view angle can be checked together in a quick and simple way, i.e. it is possible to judge in a quick and simple manner whether the endoscope tested is defective or in an acceptable state within the tolerances predetermined by the pattern. With the apparatus according to the invention, tests of endoscopes can be carried out by service employees without previous time-intensive training in a location at a customer's.

In a preferred embodiment, the pattern of the test pattern comprises a circular reference line as nominal value for the ideal viewing direction and for the ideal field of view angle, and a tolerance field, which is formed by rings that are arranged on both sides of the reference line.

By this embodiment of the test pattern, a check of the state of the viewing direction and of the field of view angle that is particularly simple to perform is allowed, because the testing person merely needs to orientate himself or herself by means of simple geometrical patterns. The reference line corresponds to the outer edge of the field of view to be observed through an ideal endoscope.

In another preferred embodiment, the test pattern comprises a pattern, which allows a check of the image quality.

By this embodiment, in addition to the common check of the viewing direction and of the field of view angle, at the same time a check of the image quality, i.e. the image sharpness by means of a geometrical pattern is made possible. The pattern for checking the image quality can be formed by an arrangement of line patterns of different line thickness on the test pattern, these line patterns being such arranged on the test pattern that the line patterns in the image center and at the image edge of the region of the test pattern observable by an ideal endoscope can be recognized. Preferably, the pattern comprises a periodical repetition of line patterns of different line thickness, so that these line patterns are observable at the image edge of the region of the test disk observable by an ideal endoscope can be recognized over the entire circumference of the image edge.

In another preferred embodiment, the first supporting device and the second supporting device can be positioned relative to each other, so that the relative position of the test pattern is endoscope-specifically adjustable with respect to the endoscope.

Instead of connecting the supporting device for the endoscope and the supporting device for the test pattern immovably to each other, as in the known apparatus of the prior art, the apparatus according to the invention provides to configure the supporting device for the endoscope and the supporting device for the test pattern positionable relative to each other, i.e. in a movable fashion, so that the relative position of the test pattern to the endoscope in dependency on endoscope-specific data of the endoscope to be tested is definedly adjustable. This offers, advantageously, the possibility of positioning the test pattern for all existing types of optical systems of endoscopes of the most different basic data such that always the same section of the test pattern is seen through the endoscope optic, so that deviations from the nominal state can be realized more easily. While the first supporting device and/or the second supporting device are positioned corresponding to the endoscope-specific data, e.g. by means of positional values that can be taken from a table, a procedure which is simple to learn even without time-intensive training, also the check of the basic data of different endoscopes is possible in a quick and easy manner because always the same features of the test pattern independent of the endoscope tested have to be evaluated. The apparatus according to the invention is, moreover, universally applicable for all existing endoscopes with the most different endoscope optics and can also be extended onto endoscope optics which, up to now, do not exist.

In a preferred embodiment, the distance between the test pattern and the endoscope is adjustable.

It is herein advantageous that, with the apparatus, a plurality of different endoscopes can be tested, which differ from each other by their predetermined field of view angle.

In another preferred embodiment, an angle between a normal line of the test pattern and the longitudinal direction of the endoscope can be adjusted.

It is herein advantageous that, with the apparatus according to the invention, a plurality of the most different endoscopes can be tested, which differ from each other by their predetermined viewing direction.

In another preferred embodiment, positional values for positioning the test pattern and/or the endoscope are allocated to endoscope-specific data of the endoscope.

The use of positional values for inserting the endoscope into the apparatus and/or for positioning the test pattern further facilitates the handling of the apparatus. The positional values can e.g. be listed in a table and can be registered as positional marks in the apparatus.

In a further preferred embodiment, the first supporting device comprises at least one first support displaceable on a first rail in longitudinal direction, the rail extending in longitudinal direction of the endoscope.

This measure has the advantage that also the endoscopes to be tested themselves can be positioned in a suitable way in the apparatus. In that way, the apparatus according to the invention is also suitable for testing endoscopes having shafts of different lengths. In particular in connection with the measure mentioned before, in which the angle between the normal line of the test pattern and the longitudinal direction of the endoscope is data-specifically adjustable, it is advantageously ensured by this measure that, even with differently long endoscope shafts, the normal line of the test pattern is always congruent with the optical axis of the viewing direction of the endoscope because the tip of the endoscope is always located at a defined point in the apparatus.

It is further preferred if the support supports the endoscope in a predetermined rotary position with respect to a longitudinal axis of the endoscope for fixing the endoscope.

In particular for endoscopes with oblique viewing optic, this measure ensures that the viewing direction of the endoscope is, if possible, vertical on the test pattern.

In another preferred embodiment, the first rail comprises a first positioning scale and the first support comprises a first scale rider that is axially displaceable on the first rail for axial positioning of the support.

By the embodiment already mentioned before of the first supporting device with a rail and a support displaceable thereon, a continuously adjustable positioning of the endoscope is achieved, whereby the apparatus is suitable for all existing lengths of endoscopes. By means of the positioning scale provided on the rail and the scale rider that is displaceable on the rail, now a positioning of the respective endoscope can be carried out by means of tabled values in a way that is particularly simple to handle. For example, for all existing different endoscopes, positional values in the form of numbers or letter-number-combinations can be listed in a table, wherein the positioning scale comprises these positioning values as markers. The scale rider can, further, comprise a vernier or the like for a fine adjustment of the position of the endoscope.

In a corresponding preferred embodiment, the second supporting device that supports the test pattern comprises a second support that is displaceable on a second rail in longitudinal direction of the rail.

By means of this support movable in longitudinal direction, now, the distance between the test pattern and the distal end of the endoscope can be adjusted in a simple to handle manner, and the distance, again, is continuously adjustable to any different endoscopes.

Also herein, it is preferred if the second rail comprises a second positioning scale and the second support comprises a scale rider that is displaceable on the second rail for axial positioning the second support on the second rail.

In that way, the distance between the test pattern and the distal end of the endoscope can be exactly adjusted by means of tabled values, by adjusting the axial position of the support of the test pattern to the tabled value accordingly.

In another preferred embodiment, the first rail and the second rail are connected with each other via a rotary joint.

Compared to the apparatus known in the prior art that comprises three bores for inserting the endoscope shafts for the test of endoscopes of different viewing directions, the embodiment of the connection of the two rails with a rotary joint according to the invention has the advantage that the possibility of a continuous angle adjustment between the two supporting devices is given, whereby endoscopes with any viewing direction can be tested.

It is here further preferred if a third positioning scale for adjusting the angle between the first rail and the second rail is circumferentially arranged at the rotary joint.

Like for the positioning scales of the first supporting device and the second supporting device, it is here also advantageous that the defined angle adjustment between the test pattern and the endoscope that is required for the respective endoscope can be done by means of tabled values and, thus, is particularly simple in handling.

It is further preferred if a set disk is arranged at the rotary joint, the set disk comprising the third positioning scale, and which is rotatable relative to the first rail and relative to the second rail.

By this measure, the entire circumference of a set disk can advantageously be equipped with a positioning scale, wherein, by turning the set disk, first of all, a basic adjustment and then, by pivoting the second rail relative to the set disk, the angle between the first and the second rail can be adjusted.

In another preferred embodiment, the test pattern comprises a pattern that allows a check of the viewing direction, of the field of view angle and/or of the image quality.

In this embodiment of the test pattern, the essential basic data of an endoscope and/or its deviations beyond predetermined tolerances can be quickly and easily determined.

In another preferred embodiment, the apparatus further comprises an illumination light test device for testing a light conducting system of the endoscope to be tested.

By means of this measure, the flexibility of the apparatus according to the invention is further increased, as also an illumination light test of the light conducting system of the endoscope can be carried out.

In order to be able to carry out the illumination light test by means of construction that is simple in design and simple in handling, the illumination light test device comprises preferably a photodetector that is movable into a position in front of the light emerging side of the endoscope and that is connected with a displaying device for displaying the light intensity.

In order to further facilitate the illumination light test and to make same easily evaluable even for staff that is not technically trained, the displaying device comprises a calibration device, e.g. a potentiometer, by means of which the displaying device is adjustable to a reference value.

With the same light source that is used for the illumination light test of the endoscope, first, the photodetector can be irradiated directly, i.e. without that the light is conducted through the endoscope, and the displaying device can be calibrated to a predetermined reference value. After that, with the same light source, the light is directed onto the photodetector through the light conducting system of the endoscope, and the person carrying out the test can then read the actual value of the light intensity and compare same with a nominal value in a table.

In order to further facilitate the reference measuring, the illumination light test device comprises preferably a light cable connection for connecting a light cable, wherein the photo detector can be brought into a position in which it is arranged adjacently to the light cable connection.

In another preferred embodiment, the photo detector is fixed at a third supporting device, which comprises a support pivotably arranged at an arm that is connected with the second rail.

By means of this measure, the illumination light test device is advantageously integrated in the second supporting device for the test pattern, and the photodetector can advantageously simply be moved in front of the distal end of the endoscope to be tested and in front of the light cable connection for the reference measuring. By fixing the support at the second rail that is pivoted relative to the first rail corresponding to the viewing direction of the endoscope, also the light of the endoscope orthogonally hits the photodetector.

Further features and advantages can be taken from the following description and the enclosed drawings.

It is to be understood that the features mentioned above and those yet to be explained below can be used not only in the respective combinations indicated, but also in other combinations or in isolation, without leaving the scope of the present invention.

BRIEF DESCRIPTION OF THE DRAWINGS

An embodiment of the invention is shown in the drawings and will be explained in more detail in the description below with reference to same. In the drawings.

DETAILED DESCRIPTION OF THE DRAWINGS

Figure 1:
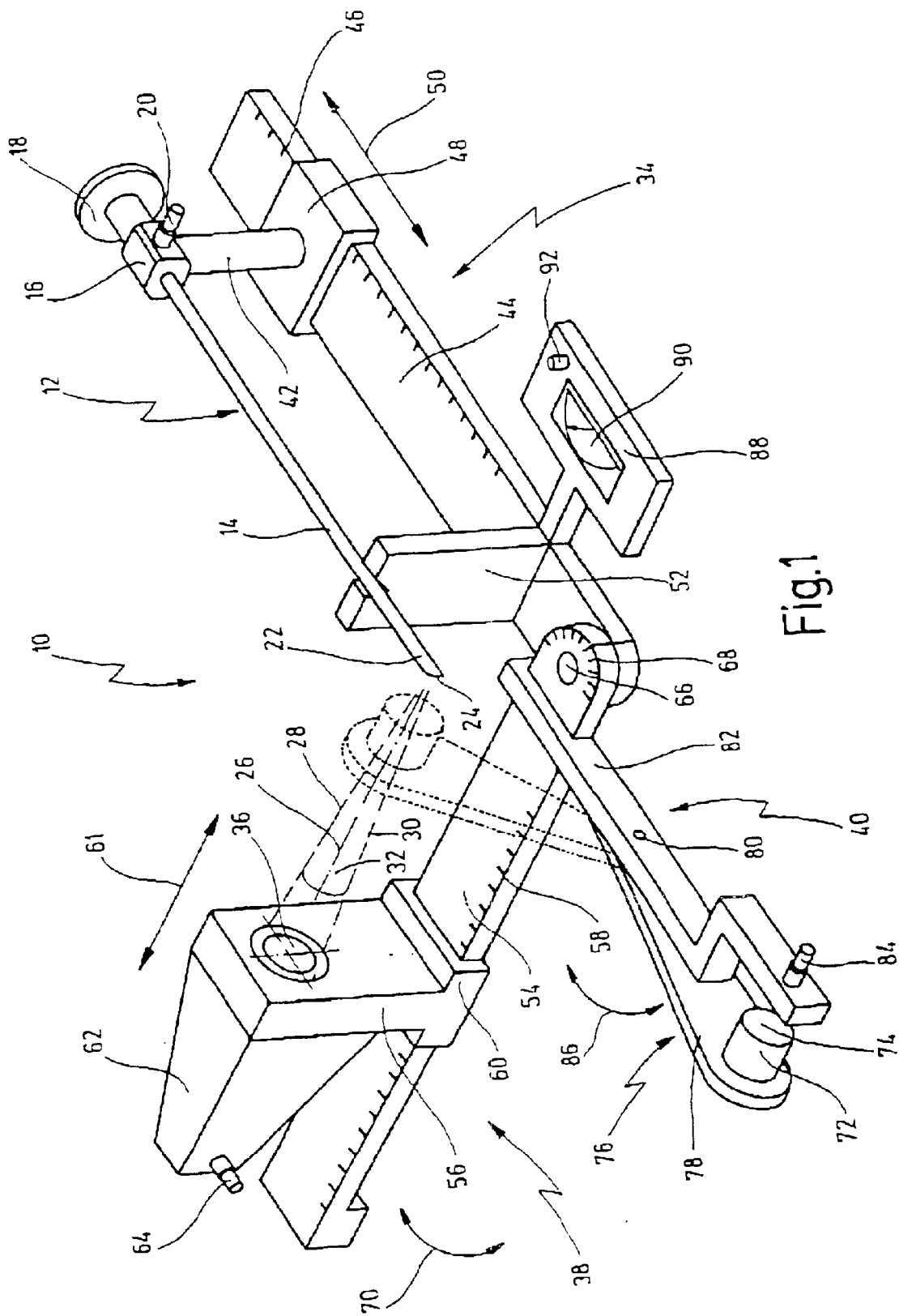
FIG. 1 shows a schematic total view of an apparatus for testing the state of the optical system of an endoscope.

In FIG. 1, an apparatus is shown that is labeled with the general reference numeral 10 for testing the state of the optical system of an endoscope 12. Apparatus 10 is altogether transportable and can be put onto a table.

By means of apparatus 10, the state of the optical system of endoscope 12 can be tested in a "good-bad"-estimation, i.e. whether the actual state of endoscope 12 still fulfills the nominal values predetermined in its manufacturing or whether the actual values deviate so far from the nominal values that endoscope 12 does not fulfill the quality requirements anymore. The viewing direction and the field of view angle of the optical system of the endoscope as well as the image quality, i.e. the image sharpness or the contrast of the image, are checkable, the check of the image quality being possible in the image center and in outer regions of the image. Furthermore, the light conducting system of endoscope 12 can be tested.

Before apparatus 10 is described in more detail, first of all, endoscope 12 will be briefly described. Endoscope 12 comprises a longitudinal rigid shaft 14, in which the optical system is arranged in the form of a relay rod lenses system or of an ordered glass fiber bundle. At the proximal end of shaft 14, endoscope 12 comprises an eyepiece housing 16, onto which an eyepiece cup 18 adjoins. The optical system of endoscope 12 also comprises the lenses in eyepiece housing 16 and/or in eyepiece cup 18 as well as objective lenses, if any, at the distal end of shaft 14.

At eyepiece housing 16, further, a light cable connection 20 is arranged for connecting a light cable not shown of a light source not shown. Correspondingly, endoscope 12 comprises a light conducting system that extends through shaft 14 in the form of disordered optical fibers, by means of which light is conducted from an external light source over light cable connection 20 up to a distal tip and/or of a distal end 22 of shaft 14, from where it then emerges from shaft 14.

Distal end 22 of shaft 14 shows, in the embodiment shown of endoscope 14, a beveled front surface 24, which forms, at the same time, the light inlet and/or the light outlet end of endoscope 12. Beveled front surface 24 indicates in FIG. 1 that endoscope 12 comprises an oblique view optic, i.e. a viewing direction 26 that is indicated by a dot-dash line runs obliquely to the longitudinal direction of endoscope 12, which is defined by the longitudinal direction of shaft 14. In the embodiment shown, endoscope 12 has a 90°-optic, i.e. viewing direction 26 runs orthogonally to the longitudinal axis of endoscope 12. Also the light that emerges from distal front surface 24 through the light supplying system of endoscope 12 is radiated with its main direction into the direction of viewing direction 26.

Viewing direction 26 in FIG. 1 represents only the axis of symmetry and/or the optical axis of the field of view of endoscope 12. Outer limits of the field of view of the optical system of endoscope 12 are indicated by discontinuous lines 28 and 30. The field of view can be described by an envelope of cone, the cone angle of which is the field of view angle 32 of the optical system of endoscope 12, which is besides viewing direction 26 relative to the longitudinal direction of endoscope 12 a further basic data of endoscope 12.

In the following, apparatus 10 is described in more detail.

Apparatus 10 comprises as main assembly groups a first supporting device 34 for endoscope 12, a test pattern 36 and a second supporting device 38 for test pattern 36. Furthermore, apparatus 10 comprises an illumination light test device 40 for testing the light conducting system of endoscope 12.

First supporting device 34 comprises a first support 42. Support 42 is arranged on a rail 44 and displaceable in the longitudinal direction of rail 44. On rail 44, a positioning scale 46 is provided, which is shown in FIG. 1 only schematically and coarsely. Support 42 comprises, at its base, a scale rider 48 that is axially displaceably arranged on rail 44. Scale rider 48 is, according to a double arrow 50, displaceable along rail 44.

Positioning scale 46 can be formed in different ways. For example, positioning scale 46 can be a length scale with millimeter scale or a scale that indicates at every scale line a combination of numbers or of letters and numbers. Scale rider 48 can be equipped with a marker not shown in the form of a line, with a vernier, if necessary with a magnifier, so that scale rider 48 can be exactly positioned at a defined point on rail 44. The positioning of scale rider 48 on rail 44 by means of positioning scale 46 is carried out herein by means of tabled values, i.e. for each endoscope and/or for each type of endoscope of a certain item number, it can be seen from a table joined to apparatus 10, at which point scale rider 48 and, thus, support 42 and, thus, again, endoscope 12 is to be positioned on rail 44 for the test to be carried out.

Support 42 comprises, for fixing endoscope 12 at support 42, a coupling that is not shown in detail, by means of which endoscope 12 is supported in a predetermined rotary position with respect to its longitudinal axis in supporting device 34. Since endoscope 12 is not rotational symmetric with respect to the longitudinal direction of endoscope 12 due to its oblique view optic, a fixation of endoscope 12 in a predetermined rotary position with respect to its longitudinal axis is required for carrying out the test.

The coupling for fixing endoscope 12 on support 42 can be a cone coupling, which is, automatically, only made possible in a certain rotary position of endoscope 12 with respect to its longitudinal axis and which is locked from the distal side at eyepiece housing 16 against a corresponding counter cone.

First supporting device 34 comprises, moreover, a further support 52 that serves merely for propping the distal region of shaft 14 of endoscope 12. Further support 52 can also be displaceable on rail 44 in the longitudinal direction of same. Further support 52, however, does not serve for positioning endoscope 12. Solely support 42 of first supporting device 42 serves for positioning endoscope 12, as described before.

Second supporting device 38 comprises a second support 56 that is displaceable on a second rail 54 in the longitudinal direction of rail 54. Second support 56 may contain in a firmly integrated fashion test pattern 36 that can be configured in the form of a card or a plate, or support 56 may comprise a box for inserting test pattern 36, so that test pattern 36 can be detached from support 56.

Second rail 54 comprises a positioning scale 58, wherein second support 56 comprises a scale rider 60 that is axially displaceable on second rail 54, by means of which second support 56 can be axially positioned on second rail 54. Scale rider 60 and, thus, second support 56 and, thus, test pattern 36 can, in that way, be displaced along second rail 54 according to a double arrow 61 and can be positioned at a corresponding point.

By means of positioning scale 58, thus, the distance between test pattern 36 and endoscope 12, more precisely, distal end 22 and/or front surface 24 can be endoscope-specifically adjusted. The scale of positioning scale 58 and the configuration of scale rider 60 can herein correspond to the scale of positioning scale 46 and the configuration of scale rider 48. Positioning scale 58, however, is different from positioning scale 46 in view of the indicated positional values in order to prevent confusions between positioning scale 46 and positioning scale 58 when, on the one hand, endoscope 12 is positioned, and, on the other hand, positioning test disk 36 is positioned.

Again, for each endoscope 12 to be tested and/or for each type of endoscope, a positional value is to be taken from the table joined to apparatus 10, to which scale rider 60 can be adjusted on positioning scale 58.

Support 56 for test pattern 36 further comprises a housing 62 at which a light cable connection 64 is provided, onto which a light cable not shown can be connected in order to illuminate test pattern 36 from its rear side. To this end, test pattern 36 is transparently configured, in the kind of a ground-glass screen.

In apparatus 10, further, an angle is adjustable between a normal line of test pattern 36, i.e. of the perpendicular standing on the plane of the test pattern, and the longitudinal direction of endoscope 12.

To this end, first supporting device 34 and second supporting device 38, i.e. more precisely, first rail 44 and second rail 54 are connected with each other via a rotary joint 66.

At rotary joint 66, a set disk not shown is arranged, comprising a circumferentially arranged positioning scale 68 for adjusting the angle between first rail 44 and second rail 54.

The markers may comprise angle indications or, again, numbers or letter-number-combinations. The corresponding positioning angle and/or the positional value of positioning scale 68 is allocated to each endoscope and/or type of endoscope to be tested in the table already mentioned, so that the predetermined table value can be adjusted at the set disk and/or at rotary joint 66.

While the adjustment of the distance of test disk 36 from endoscope 12 considers the different field of view angles of different endoscopes and/or types of endoscopes, the adjustment of the angle between the normal line of test pattern 36 and the longitudinal direction of endoscope 12 considers the different viewing directions of different endoscopes and/or of different types of endoscopes.

The set disk mentioned before, which is arranged at rotary joint 66, can further be rotatable relative to first rail 44 and to second rail 54, so that the entire circumference of the set disk can be used for positioning scale 68, by the fact that, for example, the set disk can be pre-adjusted in two or more basic positions, and, subsequently, second rail 54 can then be rotated relative to the set disk into the predetermined angle. Second rail 54 can preferably be pivoted over an angle range of 0° (second rail 54 is in linear elongation to first rail 44) up to an angle of at least 120° or more, so that also endoscopes with backward viewing direction can be tested. The angular displacement of second rail 54 relative to first rail 44 is indicated with a double arrow 70.

Altogether, thus, first supporting device 34 and second supporting device 38 can be positioned relative to each other such that the relative position of test pattern 36 to endoscope 12 is adjustable in a defined way in dependency on endoscope-specific data of endoscope 12 to be tested. The endoscope-specific data are herein preferably comprised in the table already mentioned and joined to apparatus 10, in which all endoscopes and/or types of endoscopes of the manufacturer together with the corresponding positional values for positioning scales 46 and 58 and/or 68 are listed.

Supporting device 38, supporting device 34 or rotary joint 66 are further preferably lockable in the positions determined in the table in order to prevent or to reduce the danger of undesired displacement of the position during the carrying out of the test or to facilitate the finding of the exact position.

Illumination light test device 40 mentioned before for testing the light conducting system of endoscope 12 comprises a photodetector 72 that comprises a light-sensitive front surface 74.

Photodetector 72 is fixed at a third supporting device 76 that comprises a support 78 at which photodetector 72 is fixed. Support 78 is pivotably fixed at an arm 82 via a rotary joint 80, which arm, again, is fixed at second rail 54.

At the free end of arm 82, further, a light cable connection 84 is arranged, to which a light cable not shown can be connected, which is connected with an external light source not shown. Photodetector 72 can, by pivoting support 78, on the one hand, be brought in a position, in which it is adjacent to light cable connection 84, as is shown with continuous lines in FIG. 1, and it can, by pivoting support 78, be brought in a position, in which it can be brought in front of the light emerging end, i.e. in front of front surface 24 of endoscope 12, as is shown with discontinuous lines in FIG. 1. The pivotability of support 78 is illustrated with a double arrow 86.

Illumination light test device 40 comprises further a displaying device 88 for displaying the light intensity measured by photodetector 72. Displaying device 88 is connected with photodetector 72 via a suitable electrical line not shown.

Displaying device 88 may comprise an analog display 90 or a digital display.

Displaying device 88 further comprises a calibration device 92, by means of which displaying device 88 is adjustable onto a reference value, as will be described in the following.

Figure 2:
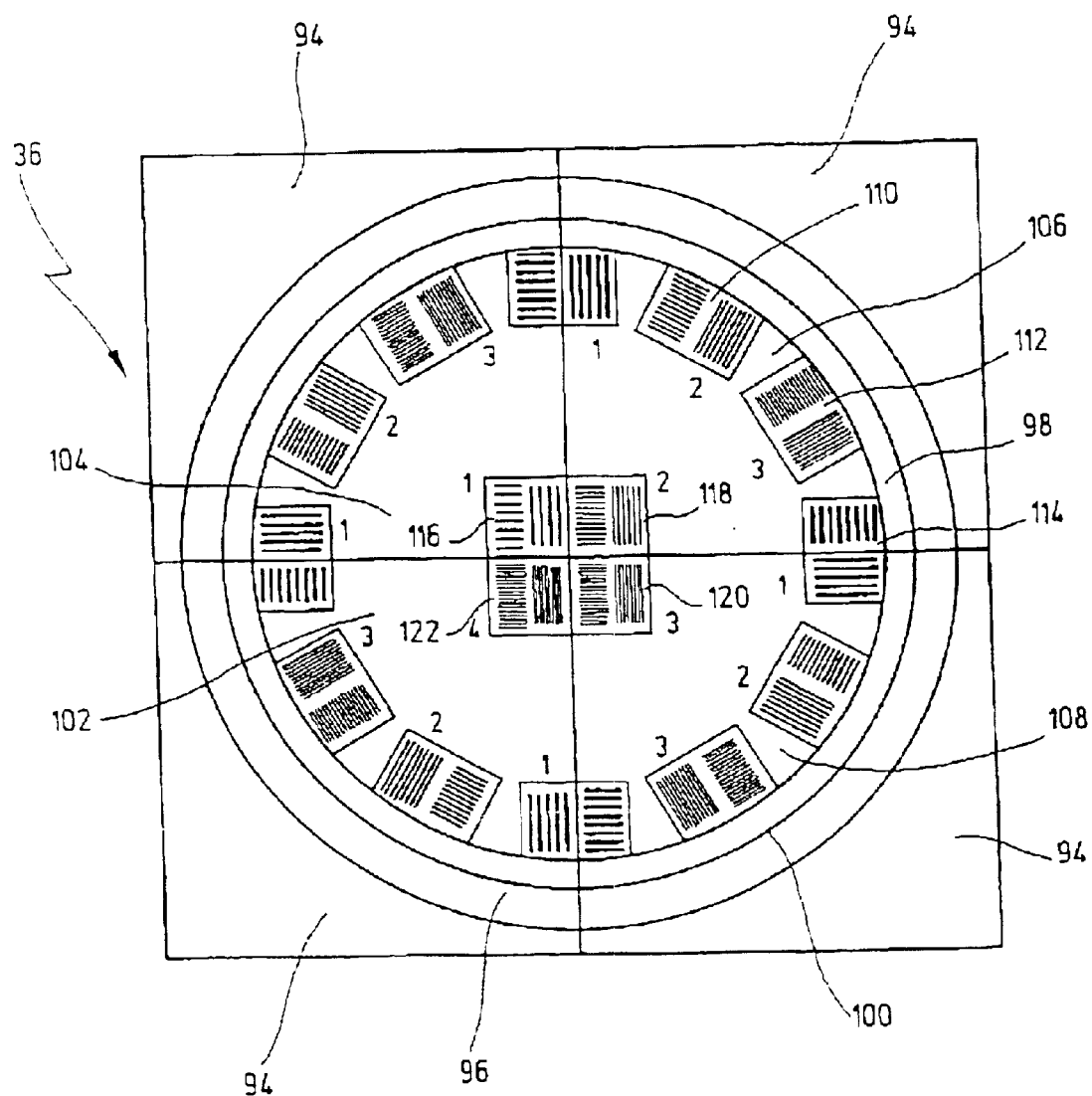
FIG. 2 shows a test picture used in the apparatus of FIG. 1 in a highly enlarged scale compared to FIG. 1.

In FIG. 2, test pattern 36 is shown in isolated fashion.

Test pattern 36 is equipped with a pattern that allows a check in the sense of a "good-bad"-estimation of the basic data of endoscope 12 to be tested within predetermined tolerance values. Test pattern 36 allows in the present case the check of viewing direction 26, of field of view angle 32 as well as of the image quality, i.e. the sharpness and the contrast of the image transmission in the image center and in the outer region of the endoscope image.

From the outward to the inward, test pattern 36 comprises a fully circumferential homogenous external sector 94, which is completely filled out with a color, e.g. red. At external sector 94, two rings 96 and 98 are adjoined, which are separated from each other by a circular reference line 100. Both rings 96 and 98 are filled out with the same color, e.g. green, over their entire circumference, in difference to external sector 94. Reference line 100 represents the nominal value for viewing direction 26 and field of view angle 32 for the ideal state of endoscope 12. Rings 96, 98 on both sides of the reference line represent tolerance fields, within same the actual viewing direction and the actual field of view angle may deviate.

The entire region of test pattern 36 within ring 98 is configured with a white background, on which in the external region of four quadrants 102–108 fields of lines 110, 112 and 114 are arranged repeating themselves from quadrant to quadrant. Fields of lines 110, 112, 114 are marked with characteristic numbers 1, 2, and 3 for different line thicknesses.

In the center of test pattern 36, four fields of lines 116–122 are arranged, which are designated with thickness characteristic numbers 1 through 4, and the line thickness of which decreases from field of lines 116 to field of lines 122.

In the following, now a method for testing endoscope 12 by means of apparatus 10 is described.

Before endoscope 12 is inserted into apparatus 10, supports 42 and 56 are positioned onto rails 44 and/or 54, and, moreover, the angle between rail 54 and rail 44 is adjusted. The positional values for positioning scale rider 48 on positioning scale 46, for positioning scale rider 60 on positioning scale 58 and the positional value for positioning scale 68 at rotary joint 66 are listed for endoscope 12 to be tested in the mentioned table and are adjusted correspondingly to the table values.

It should be mentioned in this connection that scale rider 60 is advantageously configured separately from support 56 and serves as a stop for support 56, which is arranged movably on rail 54 with an own rider. In that way, support 56 with test pattern 36 can be slid apart when carrying out the illumination light test with illumination light test device 40, without losing the positional value for the later test with test pattern 36.

After all positions have been carried out by means of the predetermined table values, endoscope 12 is fixed at support 42 and at support 52. As already mentioned before, support 42 does not only determine the axial position of endoscope 12 on first rail 44 but also its rotary position with respect to its longitudinal axis, as shown in FIG. 1. By characteristic-data-specifically positioning endoscope 12 on first rail 44, distal end 42 and/or front surface 24 comes into a position over rotary joint 66. Front surface 24 shows herein into the direction of test pattern 36. The characteristic-data-specific positioning of test pattern 36 serves for adjusting the right distance of test pattern 36 to front surface 24 of endoscope 12 that is required for the test.

If endoscope 12 is fixed at support 42, viewing direction 26 should be perpendicular to the center of test pattern 36 with a regular endoscope of this type.

After clamping endoscope 12 into first supporting device 34, the test can now start immediately. For carrying out the test, to this end, one can look with the naked eye through eyepiece 18 in order to observe test pattern 36 directly through endoscope 12, or a video camera, if existing, can be connected onto eyepiece 18, and the picture transmitted by endoscope 12 can then be shown on a screen.

If, while observing test pattern 36 the tolerance field formed by ring 98 and/or ring 96 can be seen at the entire image edge, the combination check of field of view angle 32 and viewing direction 26 of endoscope 12 within the common tolerance is in good order, i.e. endoscope 12 is, with reference to the combination of these basic characteristic data, in a good state. If one of quadrants 102–108 of the inner region and/or external sector 94 can be seen at the image edge, the combination of viewing direction 26 and field of view angle 32 of endoscope 12 is out of the common tolerance, i.e. incorrect.

By means of fields of lines 116–122, moreover, the image quality in the center of the image can be tested. The respective line pattern can be considered as to be solved, when all lines of the respective field of lines 116–122 are individually recognizable.

It can be noted down herein up to which thickness 1 through 4 the lines of fields of lines 116–122 can still be solved.

With reference to assessing the image quality, subsequently, a comparing test may be carried out with a new endoscope of the same type, whereby information about the change of the image quality of the endoscope with the age of the endoscope can be achieved.

Accordingly, as described before, the image quality at the image edge can be estimated by means of fields of lines 110–114, wherein, in the individual quadrants 102–106, the image quality should be the same from quadrant to quadrant. Also herein, again, a comparing test can be carried out with a new endoscope of the same type.

As next step, with illumination light test device 40, the check of the light conducting system of endoscope 12 can be carried out.

First of all, support 78 with photodetector 72 is pivoted into the position shown with continuous lines in FIG. 1. A light cable of a light source for carrying out the reference test is connected onto light cable connection 84. After switching on the light source, a travel of the pointer or a number is visible at displaying device 88. For calibrating displaying device 88, calibration device 92, e.g. in the form of a potentiometer, is actuated, and display 90 is adjusted, if necessary, also by adjusting the power of the light source, such that on display 90 a reference value is adjusted, e.g. 100.

The light cable is, subsequently, detached from light cable connection 84 and connected onto light cable connection 20 of endoscope 12.

Support 78 with photodetector 72 is then pivoted into the position shown in FIG. 1 with discontinuous lines. Photodetector 72 now measures the light intensity of the light conducting system of endoscope 12. From displaying device 90, a measuring value is taken that may deviate from the predetermined reference value, the reading being noted down by the user of apparatus 10. For the illumination light test, again, for each endoscope and/or for each type of endoscope, a nominal value can be taken from the table. If the current reading at display 90 is larger than the table value, the light conducting system of endoscope 12 is in a regular state.

What is claimed is:

1. An apparatus for testing the state of an optical system of an endoscope, said optical system having a viewing direction and a field of view angle, said apparatus comprising a first supporting device for supporting said endoscope, a test pattern and a second supporting device for supporting said test pattern, said first supporting device and said second supporting device being arranged such that, in use, said test pattern can be viewed through said endoscope, wherein said test pattern comprises a pattern, which allows a common check of an actual viewing direction and of an actual field of view angle of said optical system of said endoscope within tolerance values of a nominal value of said viewing direction and a nominal value of said field of view angle and wherein said pattern of said test pattern comprises a circular reference line as said nominal value for said viewing direction and as said nominal value for said field of view angle, and a tolerance field, which is formed by rings that are arranged on both sides of said reference line and which determine said tolerance values.

2. The apparatus of claim 1, wherein said test pattern comprises a pattern, which allows a check of an image quality of said optical system of said endoscope.

3. The apparatus of claim 1, wherein said first supporting device and said second supporting device can be positioned relative to each other, so that a relative position of said test pattern with respect to said endoscope is endoscope-specifically adjustable.

4. The apparatus of claim 3, wherein a distance between said test pattern and said endoscope is adjustable.

5. The apparatus of claim 1, wherein said first supporting device and said second supporting device can be positioned relative to each other, so that a relative position of said test pattern with respect to said endoscope is endoscope-specifically adjustable, and wherein an angle between a normal line of said test pattern and a longitudinal direction of said endoscope can be adjusted.

6. The apparatus of claim 1, wherein said first supporting device and said second supporting device can be positioned relative to each other, so that a relative position of said test pattern with respect to said endoscope is endoscope-specifically adjustable.

7. The apparatus of claim 1, wherein said first supporting device comprises at least one first support displaceable on a first rail in longitudinal direction, said rail extending in longitudinal direction of said endoscope.

8. The apparatus of claim 7, wherein said support supports said endoscope in a predetermined rotary position with respect to a longitudinal axis of said endoscope for fixing said endoscope.

9. The apparatus of claim 8, wherein said first rail comprises a first positioning scale and said first support comprises a first scale rider that is axially displaceable on said first rail for axial positioning of said support.

10. The apparatus of claim 1, wherein said second supporting device comprises a second support that is displaceable on a second rail in longitudinal direction of said rail.

11. The apparatus of claim 10, wherein said second rail comprises a second positioning scale, and said second support comprises a scale rider that is displaceable on said second rail for axial positioning said second support on said second rail.

12. The apparatus of claim 1, wherein said first supporting device comprises at least one first support displaceable on a first rail in longitudinal direction, said rail extending in longitudinal direction of said endoscope, and wherein said second supporting device comprises a second support that is displaceable on a second rail in longitudinal direction of said rail, and wherein said first rail and said second rail are connected with each other via a rotary joint.

13. The apparatus of claim 12, wherein a third positioning scale for adjusting an angle between said first rail and said second rail is circumferentially arranged at said rotary joint.

14. The apparatus of claim 13, wherein a set disk is arranged at said rotary joint, said set disk comprising said third positioning scale, and which is rotatable relative to said first rail and relative to said second rail.

15. The apparatus of claim 1, wherein it further comprises an illumination light test device for testing a light conducting system of said endoscope to be tested.

16. The apparatus of claim 15, wherein said illumination light test device comprises a photo detector that is movable into a position in front of a light emerging side of said endoscope and that is connected with a displaying device for displaying the light intensity.

17. The apparatus of claim 16, wherein said displaying device comprises a calibration device, by means of which said displaying device is adjustable to a reference value.

18. The apparatus of claim 1, wherein it further comprises an illumination light test device for testing a light conducting system of said endoscope to be tested, wherein said illumination light test device comprises a photo detector that is movable into a position in front of a light emerging side of said endoscope and that is connected with a displaying device for displaying the light intensity, and wherein said illumination light test device comprises a light cable connection for connecting a light cable, wherein said photo detector can be brought into a position in which it is arranged adjacently to said light cable connection.

19. The apparatus of claim 1, wherein said second supporting device comprises a second support that is displaceable on a second rail in longitudinal direction of said rail, wherein the apparatus further comprises an illumination light test device for testing a light conducting system of said endoscope to be tested, wherein said illumination light test device comprises a photo detector that is movable into a position in front of a light emerging side of said endoscope and wherein said photodetector is fixed at a third supporting device, which comprises a support pivotably arranged at an arm that is connected with said second rail.

20. An apparatus for testing the state of an optical system of an endoscope, said optical system having a viewing direction and a field of view angle, said apparatus comprising a first supporting device for supporting said endoscope;

a test pattern; and a second supporting device for supporting said test pattern, said first supporting device and said second supporting device being arranged such that, in use, said test pattern can be viewed through said endoscope, wherein said test pattern comprises a pattern, which allows a common check of an actual viewing direction and of an actual field of view angle of said optical system of said endoscope within tolerance values of a nominal value of said viewing direction and a nominal value of said field of view angle, wherein said first supporting device comprises at least one first support displaceable on a first rail in longitudinal direction, said rail extending in longitudinal direction of said endoscope and said first support supporting said endoscope in a predetermined rotary position with respect to a longitudinal axis of said endoscope for fixing said endoscope, and wherein said first rail comprises a first positioning scale and said first support comprises a first scale rider that is axially displaceable on said first rail for axial positioning of said first support.

21. The apparatus of claim 20, wherein said pattern of said test pattern comprises a circular reference line as said nominal value for said viewing direction and as said nominal value for said field of view angle, and a tolerance field, which is formed by rings that are arranged on both sides of said reference line and which determine said tolerance values.

22. The apparatus of claim 20, wherein said test pattern comprises a pattern, which allows a check of an image quality of said optical system of said endoscope.

23. The apparatus of claim 20, wherein said first supporting device and said second supporting device can be positioned relative to each other, so that a relative position of said test pattern with respect to said endoscope is endoscope-specifically adjustable.

24. The apparatus of claim 23, wherein a distance between said test pattern and said endoscope is adjustable.

25. The apparatus of claim 20, wherein said first supporting device and said second supporting device can be positioned relative to each other, so that a relative position of said test pattern with respect to said endoscope is endoscope-specifically adjustable, and wherein an angle between a normal line of said test pattern and a longitudinal direction of said endoscope can be adjusted.

26. The apparatus of claim 20, wherein said first supporting device and said second supporting device can be positioned relative to each other, so that a relative position of said test pattern with respect to said endoscope is endoscope-specifically adjustable.

27. The apparatus of claim 20, wherein said second supporting device comprises a second support that is displaceable on a second rail in longitudinal direction of said rail.

28. The apparatus of claim 27, wherein said second rail comprises a second positioning scale, and said second support comprises a scale rider that is displaceable on said second rail for axial positioning said second support on said second rail.

29. The apparatus of claim 20, wherein said first supporting device comprises at least one first support displaceable on a first rail in longitudinal direction, said rail extending in longitudinal direction of said endoscope, and wherein said second supporting device comprises a second support that is displaceable on a second rail in longitudinal direction of said rail, and wherein said first rail and said second rail are connected with each other via a rotary joint.

30. The apparatus of claim 29, wherein a third positioning scale for adjusting an angle between said first rail and said second rail is circumferentially arranged at said rotary joint.

31. The apparatus of claim 30, wherein a set disk is arranged at said rotary joint, said set disk comprising said third positioning scale, and which is rotatable relative to said first rail and relative to said second rail.

32. The apparatus of claim 20, wherein it further comprises an illumination light test device for testing a light conducting system of said endoscope to be tested.

33. The apparatus of claim 32, wherein said illumination light test device comprises a photo detector that is movable into a position in front of a light emerging side of said endoscope and that is connected with a displaying device for displaying the light intensity.

34. The apparatus of claim 33, wherein said displaying device comprises a calibration device, by means of which said displaying device is adjustable to a reference value.

35. The apparatus of claim 20, wherein it further comprises an illumination light test device for testing a light conducting system of said endoscope to be tested, wherein said illumination light test device comprises a photo detector that is movable into a position in front of a light emerging side of said endoscope and that is connected with a displaying device for displaying the light intensity, and wherein said illumination light test device comprises a light cable connection for connecting a light cable, wherein said photo detector can be brought into a position in which it is arranged adjacently to said light cable connection.

36. The apparatus of claim 20, wherein said second supporting device comprises a second support that is displaceable on a second rail in longitudinal direction of said rail, wherein the apparatus further comprises an illumination light test device for testing a light conducting system of said endoscope to be tested, wherein said illumination light test device comprises a photo detector that is movable into a position in front of a light emerging side of said endoscope and wherein said photodetector is fixed at a third supporting device, which comprises a support pivotably arranged at an arm that is connected with said second rail.

37. An apparatus for testing the state of an optical system of an endoscope, said optical system having a viewing direction and a field of view angle, said apparatus comprising a first supporting device for supporting said endoscope;
a test pattern; and
a second supporting device for supporting said test pattern, said first supporting device and said second supporting device being arranged such that, in use, said test pattern can be viewed through said endoscope, wherein said test pattern comprises a pattern, which allows a common check of an actual viewing direction and of an actual field of view angle of said optical system of said endoscope within tolerance values of a nominal value of said viewing direction and a nominal value of said field of view angle, wherein said first supporting device comprises at least one first support displaceable on a first rail in longitudinal direction, said rail extending in longitudinal direction of said endoscope, wherein said second supporting device comprises a second support that is displaceable on a second rail in longitudinal direction of said rail, and wherein said first rail and said second rail are connected with each other via a rotary joint.

38. The apparatus of claim 37, wherein said pattern of said test pattern comprises a circular reference line as said nominal value for said viewing direction and as said nominal value for said field of view angle, and a tolerance field, which is formed by rings that are arranged on both sides of said reference line and which determine said tolerance values.

39. The apparatus of claim 37, wherein said test pattern comprises a pattern, which allows a check of an image quality of said optical system of said endoscope.

40. The apparatus of claim 37, wherein said first supporting device and said second supporting device can be positioned relative to each other, so that a relative position of said test pattern with respect to said endoscope is endoscope-specifically adjustable.

41. The apparatus of claim 40, wherein a distance between said test pattern and said endoscope is adjustable.

42. The apparatus of claim 37, wherein said first supporting device and said second supporting device can be positioned relative to each other, so that a relative position of said test pattern with respect to said endoscope is endoscope-specifically adjustable, and wherein an angle between a normal line of said test pattern and a longitudinal direction of said endoscope can be adjusted.

43. The apparatus of claim 37, wherein said first supporting device and said second supporting device can be positioned relative to each other, so that a relative position of said test pattern with respect to said endoscope is endoscope-specifically adjustable.

44. The apparatus of claim 37, wherein said first supporting device comprises at least one first support displaceable on a first rail in longitudinal direction, said rail extending in longitudinal direction of said endoscope.

45. The apparatus of claim 44, wherein said support supports said endoscope in a predetermined rotary position with respect to a longitudinal axis of said endoscope for fixing said endoscope.

46. The apparatus of claim 45, wherein said first rail comprises a first positioning scale and said first support comprises a first scale rider that is axially displaceable on said first rail for axial positioning of said support.

47. The apparatus of claim 37, wherein said second supporting device comprises a second support that is displaceable on a second rail in longitudinal direction of said rail.

48. The apparatus of claim 47, wherein said second rail comprises a second positioning scale, and said second support comprises a scale rider that is displaceable on said second rail for axial positioning said second support on said second rail.

49. The apparatus of claim 37, wherein a third positioning scale for adjusting an angle between said first rail and said second rail is circumferentially arranged at said rotary joint.

50. The apparatus of claim 49, wherein a set disk is arranged at said rotary joint, said set disk comprising said third positioning scale, and which is rotatable relative to said first rail and relative to said second rail.

51. The apparatus of claim 37, wherein it further comprises an illumination light test device for testing a light conducting system of said endoscope to be tested.

52. The apparatus of claim 51, wherein said illumination light test device comprises a photo detector that is movable into a position in front of a light emerging side of said endoscope and that is connected with a displaying device for displaying the light intensity.

53. The apparatus of claim 52, wherein said displaying device comprises a calibration device, by means of which said displaying device is adjustable to a reference value.

54. The apparatus of claim 37, wherein it further comprises an illumination light test device for testing a light conducting system of said endoscope to be tested, wherein said illumination light test device comprises a photo detector that is movable into a position in front of a light emerging side of said endoscope and that is connected with a displaying device for displaying the light intensity, and wherein said illumination light test device comprises a light cable connection for connecting a light cable, wherein said photo detector can be brought into a position in which it is arranged adjacently to said light cable connection.

55. The apparatus of claim 37, wherein said second supporting device comprises a second support that is displaceable on a second rail in longitudinal direction of said rail, wherein the apparatus further comprises an illumination light test device for testing a light conducting system of said endoscope to be tested, wherein said illumination light test device comprises a photo detector that is movable into a position in front of a light emerging side of said endoscope and wherein said photodetector is fixed at a third supporting device, which comprises a support pivotably arranged at an arm that is connected with said second rail.

56. An apparatus for testing the state of an optical system of an endoscope, said optical system having a viewing direction and a field of view angle, said apparatus comprising
a first supporting device for supporting said endoscope;
a test pattern;
a second supporting device for supporting said test pattern, said first supporting device and said second supporting device being arranged such that, in use, said test pattern can be viewed through said endoscope, wherein said test pattern comprises a pattern, which allows a common check of an actual viewing direction and of an actual field of view angle of said optical system of said endoscope within tolerance values of a nominal value of said viewing direction and a nominal value of said field of view angle; and
an illumination light test device for testing a light conducting system of said endoscope to be tested, said illumination light test device comprising a photo detector that is movable into a position in front of a light emerging side of said endoscope and that is connected with a displaying device for displaying the light intensity.

57. The apparatus of claim 56, wherein said pattern of said test pattern comprises a circular reference line as said nominal value for said viewing direction and as said nominal value for said field of view angle, and a tolerance field, which is formed by rings that are arranged on both sides of said reference line and which determine said tolerance values.

58. The apparatus of claim 56, wherein said test pattern comprises a pattern, which allows a check of an image quality of said optical system of said endoscope.

59. The apparatus of claim 56, wherein said first supporting device and said second supporting device can be positioned relative to each other, so that a relative position of said test pattern with respect to said endoscope is endoscope-specifically adjustable.

60. The apparatus of claim 59, wherein a distance between said test pattern and said endoscope is adjustable.

61. The apparatus of claim 56, wherein said first supporting device and said second supporting device can be positioned relative to each other, so that a relative position of said test pattern with respect to said endoscope is endoscope-specifically adjustable, and wherein an angle between a normal line of said test pattern and a longitudinal direction of said endoscope can be adjusted.

62. The apparatus of claim 56, wherein said first supporting device and said second supporting device can be positioned relative to each other, so that a relative position of said test pattern with respect to said endoscope is endoscope-specifically adjustable.

63. The apparatus of claim 56, wherein said first supporting device comprises at least one first support displaceable on a first rail in longitudinal direction, said rail extending in longitudinal direction of said endoscope.

64. The apparatus of claim 63, wherein said support supports said endoscope in a predetermined rotary position with respect to a longitudinal axis of said endoscope for fixing said endoscope.

65. The apparatus of claim 64, wherein said first rail comprises a first positioning scale and said first support comprises a first scale rider that is axially displaceable on said first rail for axial positioning of said support.

66. The apparatus of claim 56, wherein said second supporting device comprises a second support that is displaceable on a second rail in longitudinal direction of said rail.

67. The apparatus of claim 66, wherein said second rail comprises a second positioning scale, and said second support comprises a scale rider that is displaceable on said second rail for axial positioning said second support on said second rail.

68. The apparatus of claim 56, wherein said first supporting device comprises at least one first support displaceable on a first rail in longitudinal direction, said rail extending in longitudinal direction of said endoscope, and wherein said second supporting device comprises a second support that is displaceable on a second rail in longitudinal direction of said rail, and wherein said first rail and said second rail are connected with each other via a rotary joint.

69. The apparatus of claim 68, wherein a third positioning scale for adjusting an angle between said first rail and said second rail is circumferentially arranged at said rotary joint.

70. The apparatus of claim 69, wherein a set disk is arranged at said rotary joint, said set disk comprising said third positioning scale, and which is rotatable relative to said first rail and relative to said second rail.

71. The apparatus of claim 56, wherein said displaying device comprises a calibration device, by means of which said displaying device is adjustable to a reference value.

72. The apparatus of claim 56, wherein it further comprises an illumination light test device for testing a light conducting system of said endoscope to be tested, wherein said illumination light test device comprises a photo detector that is movable into a position in front of a light emerging side of said endoscope and that is connected with a displaying device for displaying the light intensity, and wherein said illumination light test device comprises a light cable connection for connecting a light cable, wherein said photo detector can be brought into a position in which it is arranged adjacently to said light cable connection.

73. The apparatus of claim 56, wherein said second supporting device comprises a second support that is displaceable on a second rail in longitudinal direction of said rail, wherein the apparatus further comprises an illumination light test device for testing a light conducting system of said endoscope to be tested, wherein said illumination light test device comprises a photo detector that is movable into a position in front of a light emerging side of said endoscope and wherein said photodetector is fixed at a third supporting device, which comprises a support pivotably arranged at an arm that is connected with said second rail.

* * * * *